United States Patent [19]

Yamamoto et al.

[11] Patent Number: 5,683,374
[45] Date of Patent: Nov. 4, 1997

[54] ABSORBENT PADDING FOR UNDERGARMENTS

[75] Inventors: Masamitsu Yamamoto, Ehime-ken; Yoshihisa Fujioka, Kagawa-ken; Yoshio Ono, Ehime-ken, all of Japan

[73] Assignee: Uni-Charm Corporation, Kawanoe, Japan

[21] Appl. No.: 636,346

[22] Filed: Apr. 23, 1996

Related U.S. Application Data

[62] Division of Ser. No. 488,803, Jun. 8, 1995.

[51] Int. Cl.[6] .................. A61F 13/15; A61F 13/20
[52] U.S. Cl. ..................... 604/385.2; 604/378
[58] Field of Search .................. 604/378, 385.1, 604/379, 380, 382, 383, 385.2, 358

[56] References Cited

U.S. PATENT DOCUMENTS

| | | | |
|---|---|---|---|
| 3,481,337 | 12/1969 | Ruffo | 128/284 |
| 4,655,760 | 4/1987 | Morman et al. | 604/385.1 |
| 4,891,258 | 1/1990 | Fahrenkrug | 428/138 |
| 5,451,219 | 9/1995 | Suzuki et al. | 604/385.2 |
| 5,527,300 | 6/1996 | Sauer | 604/385.1 |

*Primary Examiner*—John G. Weiss
*Assistant Examiner*—Ki Yong O
*Attorney, Agent, or Firm*—Morrison Law Firm

[57] ABSTRACT

A liquid absorbent pad includes an elastically stretchable basic sheet upon which an absorbent core is periodically bonded. The absorbent core is bonded while the basic sheet is stretched. The absorbent core includes a structure which encourages the formation of corrugations therein when the basic sheet is released. The corrugations enable the flow of material in the troughs of the corrugations, and thereby reduce soilage of the upper surface of the absorbent core by fetal matter. The liquid absorbent pad is suitable for undergarment use in which the basic sheet includes a waist opening and a pair of leg openings. In one embodiment, the structure which encourages the formation of corrugations includes gaps between adjacent strips of absorbent material. In another embodiment, the structure is periodic regions of reduced density or rigidity. In a further embodiment, the structure includes periodic longitudinal indentations alternating on opposite sides of the absorbent pad.

8 Claims, 4 Drawing Sheets

ABSORBENT PADDING FOR UNDERGARMENTS

This is a divisional of co-pending application Ser. No. 08/488,803 filed on Jun. 8, 1995, pending.

BACKGROUND OF THE INVENTION

The present invention relates to an absorbent padding and, more particularly, to an absorbent padding suitable for use as an absorbent undergarment in diapers for incontinence, diapers for infants, training pants for infants or menstruation pads having front and rear bodies connected to each other along their transversely opposite side edges.

Conventional pants type absorbent undergarments generally have a liquid-absorbent core primarily made of fluffy pulp disposed between a top sheet and a back sheet. One version of conventional absorbent undergarments includes a liquid-absorbent core having transversely alternating troughs and crests, each extending longitudinally along the liquid-absorbent core. Such troughs and crests assure that liquid excretions flow diffusibly longitudinally along the core and thereby avoid sideways leakage of liquid excretion that might occur if liquid excretion diffusibly flows transversely along the core.

Prior art troughs and crests are formed by embossing the liquid-absorbent core, which, in turn, causes the garment to become more rigid and lose desirable pliability. The rigidity caused by the embossing treatment leads to discomfort of the wearer.

In addition, the top sheet (the inner sheet closest to the wearer's body) covering a top surface of the liquid absorbent core remains substantially flat despite the corrugation of the liquid-absorbent core. As a result of the top sheet of the core assembly lacking the desirable corrugated configuration, liquid fecal material not passing through the top sheet can diffusibly flow sideways and cause undesirable leakage.

It is also well known to wrinkle or crease the top sheet of conventional absorbent undergarments so that the top sheet itself may be corrugated and to cover the liquid-absorbent core with this corrugated top sheet. While this known technique has been found to be effective to some degree in preventing liquid fecal material from diffusibly flowing sideways, the configuration formed by this technique has other disadvantages.

Chief among them is that the wrinkled or creased top sheet floats at its respective crests away from the top surface of the liquid-absorbent core. Consequently, the absorptive power for liquid excretion is significantly deteriorated because the top sheet is out of contact with the liquid-absorbent core.

OBJECTS AND SUMMARY OF THE INVENTION

It is an object of the present invention to provide a disposable absorbent padding material which overcomes the drawbacks of the prior art.

It is a principal object of the invention to solve the problems, as mentioned above, by configuring an absorbent pad separately of a basic sheet and bonding this absorbent pad to the inner surface of the basic sheet to obtain the desired corrugated configuration.

It is an object of this invention to provide a disposable absorbent pad formed with a plurality of transversely alternate troughs and crests extending longitudinally.

Briefly stated, the present invention provides a liquid absorbent pad which includes an elastically stretchable basic sheet upon which an absorbent core is periodically bonded. The absorbent core is bonded while the basic sheet is stretched. The absorbent core includes a structure which encourages the formation of corrugations therein when the basic sheet is released. The corrugations enable the flow of material in the troughs of the corrugations, and thereby reduce soilage of the upper surface of the absorbent core by fecal matter. The liquid absorbent pad is suitable for undergarment use in which the basic sheet includes a waist opening and a pair of leg openings. In one embodiment, the structure which encourages the formation of corrugations includes gaps between adjacent strips of absorbent material. In another embodiment, the structure is periodic regions of reduced density or rigidity. In a further embodiment, the structure includes periodic longitudinal indentations alternating on opposite sides of the absorbent pad.

According to an embodiment of the invention, there is provided a liquid absorbent pad comprising: a first substantially planar element, at least part of the first substantially planar element being an absorbent material, a second substantially planar element, the second substantially planar element being stretchable, the first substantially planar element including parallel portions having one of a greater flexibility and a lower rigidity than a remainder thereof, the first planar element being fastened to the second planar element at a plurality of places while the second substantially planar element is stretched, whereby, when the second substantially planar element is released, the first substantially planar element is deformed into corrugations along the parallel portions having a greater flexibility.

According to a feature of the invention, there is provided a method for making a liquid absorbent pad comprising: applying a tension for stretching a first substantially planar element along an axis, forming parallel portions in a second substantially planar element, having one of reduced rigidity and increased flexibility compared to a remainder thereof, periodically affixing the second substantially planar element to the first substantially planar element, and releasing the tension, whereby the second substantially planar element is corrugated along the parallel portions.

According to a further feature of the invention, there is provided a liquid absorbent undergarment comprising: an elastically stretchable material basic sheet having an inner surface, a front body and a rear body, the sheet including a waist opening and a pair of leg openings, an absorbent pad intermittently bonded to the inner surface across the front and the rear bodies, and the absorbent pad including a plurality of transversely alternate troughs and crests each extending longitudinally of the pad.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENTS

The object of the present invention is achieved, by an absorbent pad which is bonded intermittently to an inner surface of an exterior basic sheet. The basic sheet, in turn, is made of a fibrous nonwoven fabric which is elastically stretchable at least in length and width.

When configured as an undergarment such as an underpants, the basic sheet is formed with a waist opening and a pair of leg openings. The absorbent pad is intermittently bonded to the inner surface of the basic sheet, across the front and rear with the absorbent pad having a plurality of transversely alternate troughs and crests each extending longitudinally along the absorbent pad.

Liquid excretion diffusibly flows longitudinally along the troughs of the absorbent pad and is absorbed. Liquid fetal material also flows along the troughs but the invention keeps most of the fecal material away from the tops of the respective crests. Hence, the present invention substantially avoids the smearing of liquid fetal matter on top surface of the absorbent 'pad.

Figure 1:
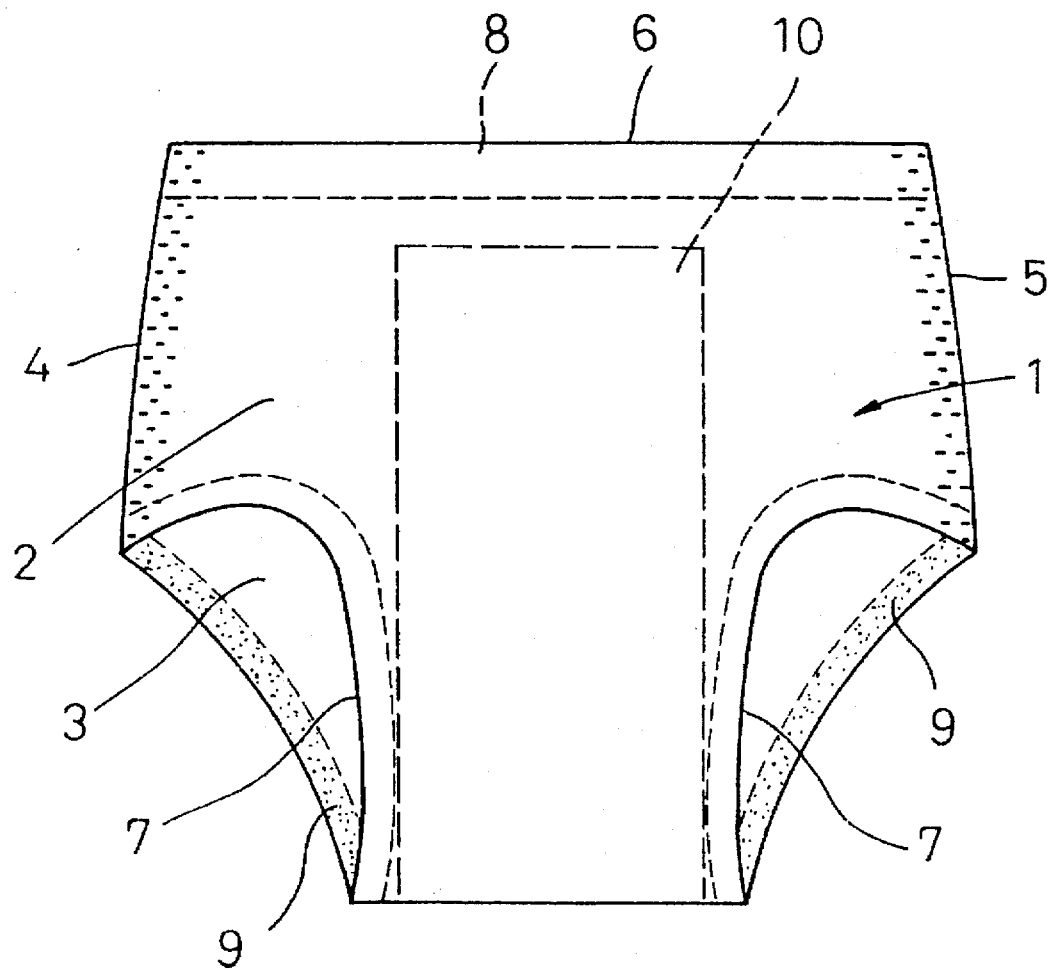
FIG. 1 is a front view of an undergarment according to an embodiment of the invention.
Figure 2:
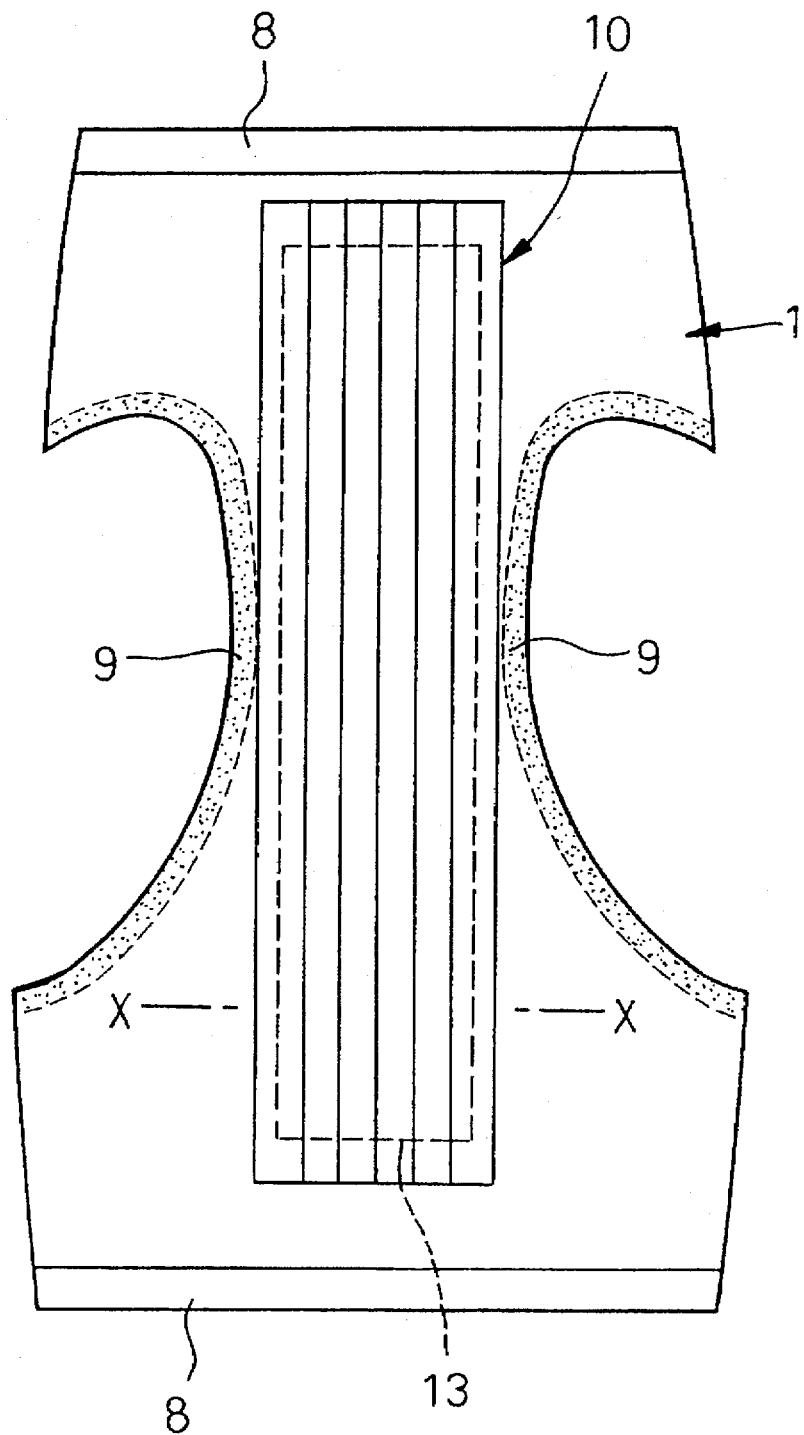
FIG. 2 is a plan view showing an inside of the undergarment of FIG. 1 as developed.
Figure 3:
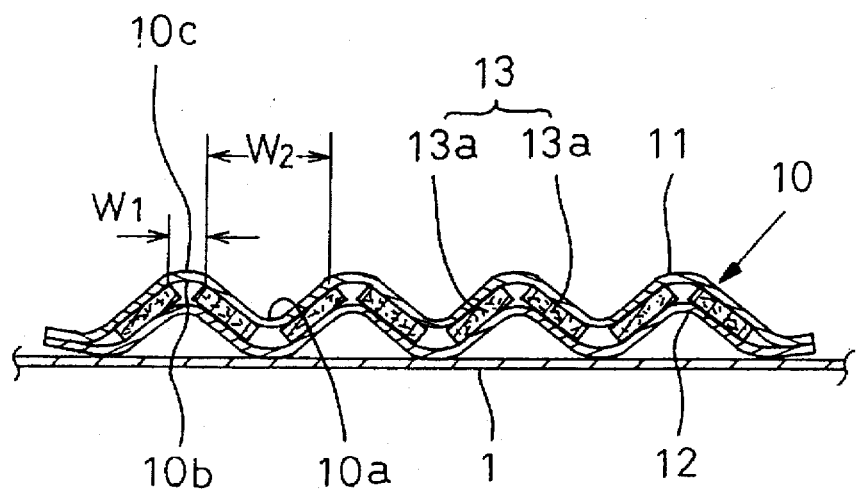
FIG. 3 is a sectional view showing an absorbent pad as taken along a line X—X in FIG. 2.

Referring to FIGS. 1 through 3, an undergarment according to an embodiment of the invention, shown generally at 20, includes a basic sheet 1. Basic sheet 1 is made up of a front 2 bonded to a rear body 3 along their transversely opposite side edges 4 and 5 to form a waist opening 6 and a pair of leg openings 7. Basic sheet 1 is cut from a fibrous nonwoven fabric which is elastically stretchable in length and width. It is preferable that the fabric be more elastically stretchable in width than in length.

Basic sheet 1 defining the front and rear bodies 2 and 3 may be cut from a web including thermo-crimpable synthetic fibers subjected to a known intertwining treatment under water jets. Alternatively, the web may have fibers dot-bonded together by heating under high pressure.

A circumferentially stretchable tape-like elastic member 8 is attached to an inner peripheral surface of waist opening 6. For an aesthetic effect, the elastic member 8 may have a color that is different from that of the basic sheet 1 defining the front and rear bodies 2 and 3, since the color of the elastic member 8 is visible through basic sheet 1.

Commonly known synthetic hot melt resins having rubber-like elasticity in their cured state can be continuously applied to the inner peripheral surface of each leg opening 7 without leaving a margin around the outer edge. This aids in the formation of a tape-like elastic zone 9 having a stretch stress of from about 50 to about 130 grams In this manner, the tape-like elastic zone 9 around the leg openings 7 has a stretch stress higher than in the elastic-member-free portion of the basic sheet 1. Values of stretch stress are measured by cutting off a strip of the same size as tape-like elastic zone 9 from the portion of the basic sheet 1 having no hot melt type synthetic resin applied thereto and performing comparative measurements.

An alternative to using the above noted resins, a rubber or an elastomeric compound, preferably in a liquid- or gel-state can be used. A rubber or elastomeric compound that exhibits an elasticity in its cured state can also be used. If such rubber or elastomeric compound requires heat treatment for its generation or application, it must retain elasticity upon cooling.

To apply liquid-state elastic material to the inner peripheral surface of each leg opening 7 without leaving any margin around the outer edge thereof, the basic sheet 1 one of the above resins is applied to define a relatively large tape-like elastic zone 9 before basic sheet 1 is cut to form leg openings 7. The cut to form leg openings 7 is made along a cutting line lying within the applied zone. Thus, any excess resin is removed with the material of basic sheet 1 being removed to form leg openings 7.

Tape-like elastic zone 9 on the inner peripheral surface of leg openings 7 may be coated with a nonwoven fabric of stretchable fibers to add comfort to the wearer, particularly if the feel of elastic zone 9 against the wearer might be uncomfortable. Alternatively, elastic zone 9 can be formed on the outer peripheral surfaces of leg openings 7.

The elastic material composed of the above noted resins should preferably be of a color different from that of the basic sheet 1 which defines front and rear bodies 2 and 3. The elastic material may be used to form tape-like elastic zone 9 and thereby to rim leg openings 7 for an aesthetic effect as in the case of waist opening 6.

Referring to FIG. 3, a cross section, generally identified by 16, shows absorbent pad 10 disposed on an inner surface of basic sheet 1. Absorbent pad 10 is affixed by intermittent bonding (preferably dot-bonding) by adhesive or welding. Absorbent pad 10 includes a plurality of transversely alternate troughs 10a and crests 10b, each extending longitudinally along absorbent pad 10. To avoid smearing the wearers with liquid fecal material clinging to the surface of absorbent pad 10, top surface 10c of each crest 10b preferably has a width W1 narrower than a width W2 of trough 10a defined between each pair of adjacent top surfaces 10c. The total area of top surfaces 10c is preferably less than one-third of a total surface area of absorbent pad 10. Troughs 10a and crests 10b are formed by contraction of basic sheet 1 after absorbent pad 10 is bonded to basic sheet 1. In this process, basic sheet 1 is transversely tensioned.

Troughs 10a and crests 10b are formed over a liquid-absorbent core 13. Liquid-absorbent core 13 is made up of a plurality of narrow liquid-absorbent core strips 13a transversely spaced from one another. A liquid permeable top sheet 11 is disposed over core strips 13a. A liquid permeable back sheet 12 is disposed below core strips 13a. Top sheet 11 and back sheet 12 are made of a fibrous nonwoven fabric. In effect, the gaps between adjacent core strips 13a forms regions of low rigidity which encourages peaks and valleys of the corrugations of FIG. 3 to form in these locations when basic sheet 1 contracts during fabrication.

Figure 4:
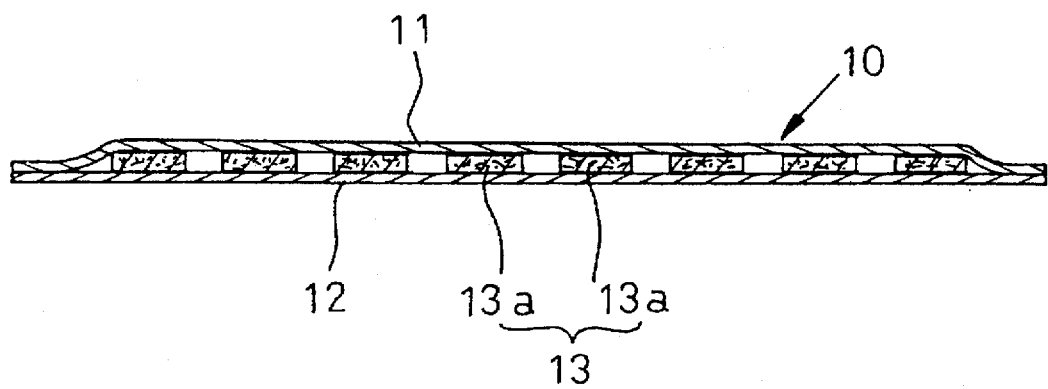
FIG. 4 is a sectional view showing the absorbent pad of FIG. 2 that includes a corrugated configuration.

Referring now to FIG. 4, prior to being affixed to basic sheet, and shrunk into the corrugations shown in FIG. 3, absorbent pad 10, shown in cross section generally at 17, is a flat sheet. Core strips 13a are fixed in place between top sheet 11 and back sheet 12 using adhesive or welding. Top sheet 11 and back sheet 12 are bonded together about their outer perimeters to confine liquid-absorbent core 13 between them.

Figure 5:
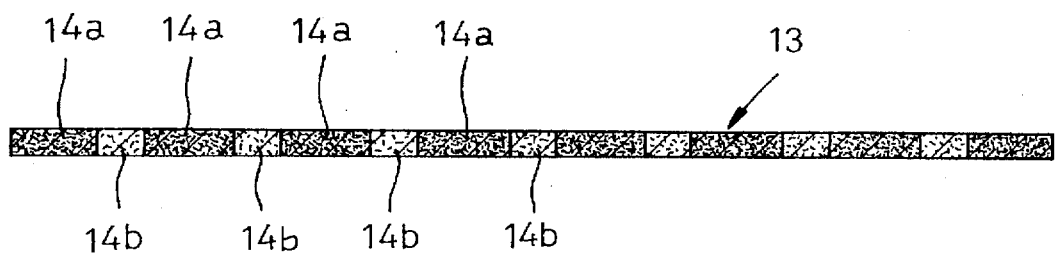
FIG. 5 is a sectional view showing another embodiment of an absorbent pad as taken along a line X—X in FIG. 2.

Referring now to FIG. 5, generally at 18, a further embodiment of the invention includes a one-piece liquid-absorbent core 13. One-piece core 13 is made up of a plurality of sections 14a having a high density or a high rigidity, alternating with a plurality of sections 14b having a low density or a low rigidity. Sections 14a and 14b extend longitudinally of the core 13.

In a manner similar to the prior embodiment, low density sections 14b provide preferred locations for the formation of troughs 10a and crests 10b, so that the final form of the embodiment of FIG. 5 is the same as the embodiment of FIGS. 3 and 4, with troughs and crests in low density or low rigidity sections 14b, alternating with high density or high rigidity, sections 14a therebetween.

Prior to affixing absorbent pad 10 to basic sheet 1, basic sheet 1 is held stretched. While basic sheet 1 is held stretched, absorbent core 13 is attached thereto at intermittent locations. Then, when basic sheet 1 is released, the contraction of basic sheet 1 deforms the intermittently attached absorbent pad 10 into the plurality of troughs 10a and crests 10b of FIG. 3.

Figure 6:
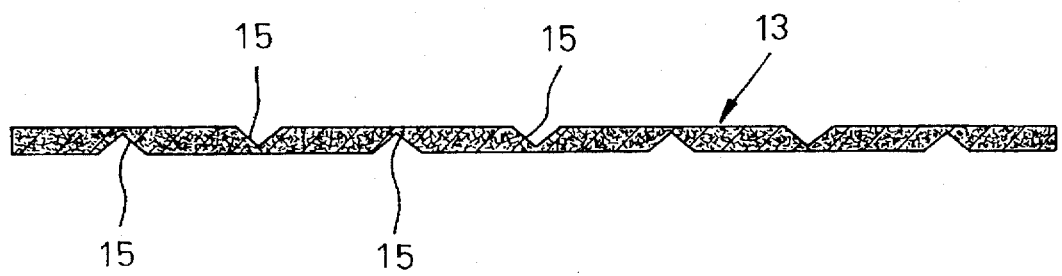
FIG. 6 is a sectional view showing further another embodiment of an absorbent pad as taken along a line X—X in FIG. 2.

Referring now to in FIG. 6, a further embodiment of a core 13, shown generally at 19, includes a plurality of compressed grooves 15 transversely spaced from one another on upper and lower surfaces, each extending longitudinally along core 13. Compressed grooves 15 provide regions of lower rigidity or increased flexibility for encouraging the formation of troughs 10a and crests 10b, upon the contraction of the basic sheet 1. Similar to the above described embodiment, basic sheet 1 is stretched while absorbent core 13 is intermittently attached thereto. Upon releasing basic sheet 1, the intermittently attached absorbent core 13 is deformed into a plurality of troughs and crests by contraction of basic sheet 1.

Cores 13 of FIGS. 5 and 6 are deformed into a corrugated configuration by being bent along the low density or low rigidity sections 14b, in the case of FIG. 5, or by being bent along grooves 15, in the case of FIG. 6. Though not shown, cores 13 shown in FIGS. 5 and 6 are also integrally disposed between top sheet 11 and back sheet 12, and grooves 15 are formed together with these sheets 11, 12.

Liquid-absorbent core 13 is made of one of, or a mixture of, thermo-crimpable synthetic fibers, fluffy pulp and high absorption polymer powders. It is preferable that the fibers of core 13 are partially fused together to provide a netlike structure. Although back sheet 12 is described as being liquid permeable, a liquid-impermeable sheet such as a water repellent fibrous nonwoven fabric or a plastic film may be also used.

With the undergarment of the invention constructed as described hereinabove, body exudates flow diffusibly longitudinally along the troughs of the absorbent pad to be absorbed thereby. Liquid fecal material also flows along the troughs below the top surface of the absorbent pad, i.e., away from the top surfaces of the crests 10b. Thus, smearing of the liquid fecal matter on the top surface of the absorbent pad is minimized. This invention not only avoids sideways leakage of material, but also allows clearance of troublesome accumulations by flow along troughs 10a. Further, possible outbreaks of skin diseases such as eruptions or sores due to liquid fecal material clinging to the wearer's skin are also minimized.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A liquid absorbent undergarment comprising:
   a basic sheet made from an elastically stretchable material, said basic sheet having an inner surface, a front body and a rear body;
   said basic sheet including a waist opening and a pair of leg openings;
   an absorbent pad intermittently bonded to said inner surface across said front and said rear bodies;
   said absorbent pad including a liquid absorbent core between a top sheet and a back sheet;
   said liquid absorbent core including a plurality of substantially parallel portions;
   a first set of said plurality of substantially parallel portions transversely spaced from one another thereby forming gaps between each adjacent pair of said first set of said plurality of substantially parallel portions;
   a second set of said plurality of substantially parallel portions forming regions between each adjacent pair of said first set of said plurality of said substantially parallel portions;
   said second set of said plurality of substantially parallel portions being lower in rigidity than said first set of said plurality of substantially parallel portions; and
   said absorbent pad including a plurality of transversely alternate troughs and crests each extending along said regions of low rigidity between each adjacent pairs of said first set of said plurality of substantially parallel portions.

2. The undergarment according to claim 1, wherein said troughs and crests are formed upon the contraction of said basic sheet after said absorbent pad has been bonded to said basic sheet while said basic sheet is tensioned transversely to said plurality of substantially parallel portions.

3. The undergarment according to claim 1, wherein:
   said second set of said plurality of parallel portions includes a first plurality of substantially parallel grooves on a first surface of said liquid absorbent core;
   said second set of said plurality of parallel portions further includes a second plurality of substantially parallel grooves disposed on an opposite second surface of said liquid absorbent core; and
   said second plurality of grooves are disposed substantially parallel to and alternating with said first plurality of grooves.

4. The undergarment according to claim 3, wherein said substantially parallel grooves are compressed into said liquid absorbent core.

5. A liquid absorbent undergarment, comprising:
   a first element;
   said first element being an absorbent pad;
   said absorbent pad including a liquid absorbent core between a top sheet and a back sheet;
   said liquid absorbent-core including a plurality of substantially parallel portions;
   a first set of said plurality of substantially parallel portions transversely spaced from one another thereby forming gaps between each adjacent pair of said first set of said plurality of substantially parallel portions;
   a second set of said plurality of substantially parallel portions forming regions between each adjacent pair of said first set of said plurality of substantially parallel portions;
   said second set of said plurality of substantially parallel portions being lower in rigidity than said first set of said plurality of said substantially parallel portions
   a second element;
   said second element being stretchable;
   said second element being conformable to a shape wearable as an undergarment;
   said first element being fastened to said second element at a plurality of places while said second element is stretched, wherein said first element is inclined to form peaks and troughs along said regions of low rigidity between each adjacent pair of said first set of said plurality of substantially parallel portions.

6. The undergarment according to claim 5, wherein said first set of said plurality of substantially parallel portions further include a plurality of liquid-absorbent core strips transversely spaced substantially parallel to each other.

7. The undergarment according to claim 5, wherein:

said second set of said plurality of substantially parallel portions includes a first plurality of substantially parallel grooves on a first surface of said liquid absorbent core;

said second set of said plurality of substantially parallel portions further includes a second plurality of substantially parallel grooves disposed on an opposite second surface of said liquid absorbent core; and said second plurality of grooves are disposed substantially parallel to and alternating with said first plurality of grooves.

8. The undergarment according to claim 7, wherein said substantially parallel grooves are compressed into said liquid absorbent core.

* * * * *